United States Patent [19]
Techiera

[11] Patent Number: 6,106,529
[45] Date of Patent: Aug. 22, 2000

[54] EPICONDYLAR AXIS REFERENCING DRILL GUIDE

[75] Inventor: Richard C. Techiera, Avon, Mass.

[73] Assignee: Johnson & Johnson Professional, Inc., Raynham, Mass.

[21] Appl. No.: 09/216,043

[22] Filed: Dec. 18, 1998

[51] Int. Cl.⁷ .................................................. A61B 17/56
[52] U.S. Cl. ............................................. 606/88; 606/87
[58] Field of Search ................................. 606/86, 87, 88, 606/89, 96, 102; 623/20

[56] References Cited

U.S. PATENT DOCUMENTS

| | | | |
|---|---|---|---|
| D. 367,706 | 3/1996 | Stalcup et al. | D24/140 |
| 4,524,766 | 6/1985 | Petersen . | |
| 4,759,350 | 7/1988 | Dunn et al. . | |
| 5,395,377 | 3/1995 | Petersen et al. | 606/88 |
| 5,417,694 | 5/1995 | Marik et al. | 606/88 |
| 5,443,518 | 8/1995 | Insall | 623/20 |
| 5,458,645 | 10/1995 | Bertin | 623/20 |
| 5,474,559 | 12/1995 | Bertin et al. | 606/89 |
| 5,540,696 | 7/1996 | Booth, Jr. et al. | 606/88 |
| 5,562,675 | 10/1996 | McNulty et al. | 606/96 |
| 5,688,280 | 11/1997 | Booth, Jr. et al. | 606/88 |
| 5,810,831 | 9/1998 | D'Antonio | 606/88 |
| 5,830,216 | 11/1998 | Insall et al. | 606/88 |

OTHER PUBLICATIONS

Thomas S. Thornhill, et al. "Revision Surgery for Failed Total–Knee Replacement"—Johnson & Johnson Orthopaedics SP2–008 (1997).

Richard D. Scott, et al. "Primary Cruciate–Retaining Procedure"—Johnson & Johnson Orthopaedics, pp. 1–55 (undated).

Richard A. Berger, M.D., et al. "Determining the Rotational Alignment of the Femoral Components in Total Knee Arthoplasty Using the Epicondylar Axis" Determining Femoral Roitation in TKA, Clinical Orthopaedics and Related Research, pp. 40–47, No. 286, Jan., 1993.

*Primary Examiner*—Michael Buiz
*Assistant Examiner*—David O. Reip
*Attorney, Agent, or Firm*—Nutter, McClennen & Fish LLP

[57] ABSTRACT

A tool and a method for laying out resection or alignment features to prepare a bone end for prosthetic joint replacement. The tool includes adjustable assemblies coupled to a main body for determining a preparatory cut to fit a prosthesis, for example by drilling positioning holes or otherwise setting one or more preparatory cuts, and further includes elements for sizing the prosthesis. The body carries a sighting, pointer or caliper assembly which aligns to or is positioned on the medial and lateral epicondyles, and aligns the body along the epicondylar axis, while one or more other assemblies determine a line, depth or other positioning component to adjust the position of the body with respect to other landmarks before anchoring the assembly and performing cuts. In prototype embodiments, the body positions a drill guide to locate positioning pin holes in the femur. Preferably, a template or one or more sets of graduations constitute a sizing jig in the tool, which may determine an offset, and the drill positioning block is coupled so that it positions drill holes on the bone end in coordination with sizing jig or other offset indicators. The device allows the surgeon to confirm or change the prosthesis size with regard to landmarks, and to visualize its fit in different translated positions. The drill holes may set a position for a standard cutting block to fit a femoral end component. Further, by manually shifting the assembly while the cortex hook contacts the anterior femoral surface, the prosthesis may be aligned with the trochlear groove of the femur to improve patellar tracking. Preferably, the tool places drill holes in position for a standard set of cutting blocks to fit a femoral end component of a prosthetic knee.

12 Claims, 3 Drawing Sheets

EPICONDYLAR AXIS REFERENCING DRILL GUIDE

CROSS-REFERENCE TO RELATED APPLICATIONS

This application is related to the patent application entitled EPICONDYLAR AXIS-FEMORAL POSITIOINING DRILL GUIDE of inventors Richard C. Techiera, Arlen D. Hanssen and Scott R. Presbrey filed of even date herewith and bearing attorney docket number 22675-159.

STATEMENTS REGARDING FEDERALLY SPONSORED RESEARCH

Not applicable.

FIELD OF INVENTION

The present invention relates to tools and jigs for laying out machine cuts to prepare a bone for receiving a correctly sized and aligned prosthetic component, such as a component of a prosthetic knee joint assembly.

BACKGROUND OF THE INVENTION

The surgical preparation of bone endings for receiving prosthetic knee joints for a total knee replacement is generally a complex procedure, particularly when ligaments remain attached, or when osteoarthritic changes to the joint have distorted the normal bone endings or the articulation geometry of the joint or bone. In general, it is necessary to determine a number of positioning pin locations, form a number of flat surface cuts, and carry out a soft tissue balancing procedure. Numerous specially aligned cuts at the bone ends are necessary in order to install the prosthetic components with correct spacing, alignment and tensioning to prevent improper kinematics from arising as the joint rotates in use, and to avoid the occurrence of accelerated wear patterns or possible joint dislocation.

The bone cuts made to effect the placement and orientation of the femoral component of the prosthesis determine and form the joint gaps in extension and flexion. The size and shape of these two gaps affect final bone orientation as well as joint tensioning and clearances. The femur must be so oriented, with respect to the cut surfaces defining the prosthesis fit, so as to satisfy numerous constraints. With respect to their effect on final orientation, the flexion gap is related to internal/external orientation of the femur, while the extension gap is related to the varus/valgus orientation of the femur.

Generally, these cuts are formed so that in extension the joint gap is perpendicular to the mechanical axis of the femur, while in flexion the joint gap is such as to place the femoral component in either neutral or external rotation to assure proper patellar tracking with the femoral component. Furthermore to fit the femoral component, the gaps created by the bone resections in both flexion and extension should be rectangular. In flexion, the relevant natural articulation surface corresponds to the tangent plane of the posterior epicondyles, and in extension, to that of the distal epicondylar surface. However, by performing A/P cuts by reference to the posterior surfaces, there is some risk of notching the anterior cortex. Thus, many surgeons set the A/P cut positions with reference to the anterior cortex. In a similar fashion, several different sequences of cuts may be utilized, generally as a matter of each surgeon's preference, to arrive at a final stage of bone preparation for attaching the femoral prosthesis. In one common approach, the fitting is done by first resecting the distal femur, then drilling positioning holes for the femoral joint component positioning pins, and subsequently placing one or more cutting blocks of a standard set of blocks, or other tool alignment assemblies, into the positioning holes to guide the necessary cuts in the femur.

Typically the fitting requires a number of measurement steps and cutting steps, often with additional small adjustment cuts to achieve a final bone preparation which will correctly orient and position the component. However it is difficult to devise a single jig which dependably sets the femoral component alignment because the necessary landmarks may be inconsistent or obscure. In general, the surgeon may have to exercise judgment as the various cuts are made. Also the steps in reaching a determination will vary depending upon the initial landmarks used for setting preliminary resections, both as a matter of the surgeon's preferred procedure and as constrained by any patient-specific features or disease.

Recently, some interest has arisen in using the epicondylar axis as a guide line, either by marking its position as a reference for confirming alignment or making slight adjustments during fitting, or as a primary landmark when disease or a previous arthroplasty have altered or obliterated the usual primary landmarks. When used to set internal/external rotation this provides improved balance of the collateral ligament tension between flexion and full extension. However, it can be awkward to determine the epicondylar axis, and while the clinical epicondylar prominence may be considered in advance of surgery, this feature varies somewhat from a true geometric center of the articulation axis. Thus, when used as a reference, the epicondylar axis is generally marked on the distal femoral cut surface, when the leg is in flexion, viewing the exposed epicondyles head-on. Thereafter, the surgeon may use the marked line to harmonize or check the preparatory cuts or axes determined by other measurement jigs and empirical offsets, such as to adjust an axis original set parallel to the posterior epicondylar tangent plane, or a fitting referenced to the trochlear groove. The resulting sequence of steps may be complex and time consuming.

Accordingly, it would be desirable to provide a tool to simplify procedures during surgery for performing preparatory bone cuts or setting alignment marks to prepare the bone to receive a prosthetic joint component aligned with respect to the epicondylar axis.

It would further be desirable to provide a tool for checking size or adjusting an offset to select an optimal size prosthesis for the particular femoral geometry.

SUMMARY OF THE INVENTION

One or more of these and other desirable features are achieved by a tool in accordance with the present invention which sets a resection or alignment feature to position a prosthetic joint component. The tool is used at the distal femoral resected surface, and includes one or more assemblies coupled to a main body for alignment with the epicondylar axis, and which set the orientation of the main body. The main body positions a cutter, e.g., includes a drill guide or saw blade guide. One or more further units may couple to the body for sizing a prosthetic component, or fixing its position, for example by locating A/P positioning holes or otherwise more fully determining or setting one or more preparatory cuts. The epicondylar alignment assemblies may include an epicondyle sighting assembly or a pointer, and the additional units may include an A/P setting jig, such as a cortex hook assembly which is mounted in such a way as to enable forced lateral translation to accommodate an asymmetry or deformity of the bone end. One or more components of the tool may slide in the central body to facilitate alignment on the bone end, and graduations on the assemblies may indicate suitable sizes for the prosthesis in view of their position on the femur or their degree of extension. Before making a determinative cut or drill hole, the body may be shifted laterally to optimize the component position for load bearing or patellar tracking. Once positioned, the body is immobilized by an impact which sets protruding barbs into the bone surface, and the holes are then drilled to accommodate the positioning pins of a standard set of cutting blocks.

DETAILED DESCRIPTION OF THE DRAWINGS

The foregoing features of this invention, as well as the invention itself, may be more fully understood from the following description of the illustrative embodiments, taken together with the drawings in which.

DETAILED DESCRIPTION OF THE INVENTION

The present invention is a tool which simplifies the procedure of preparing the distal femoral end for a prosthetic implant by allowing the surgeon to conveniently size the femur and position components in relation to the epicondylar axis using a single instrument. The mechanical arrangement of various components of the tool in a prototype embodiment 100 will be appreciated from discussion of the figures below, illustrating representative structures and their manner of use.

Figure 1:
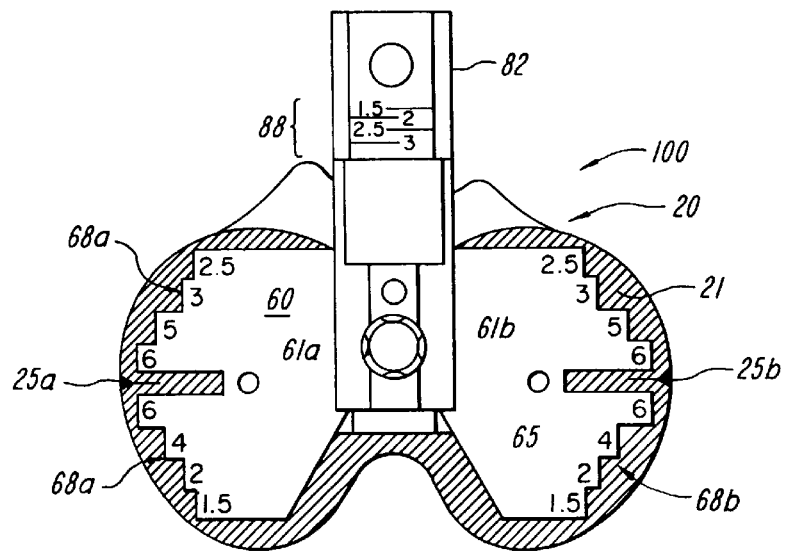
FIG. 1 illustrates one embodiment of the tool according to the present invention positioned at the distal end of a right femur.

As shown in FIG. 1, a first prototype tool 100 is intended for use during surgery, and has a body which lies across the distal resected end 21 of a femur 20, which may be either the right or left femur. By way of overview, the tool is preferably used once the surgeon has made the distal femoral cut, and includes a central body 60 which includes a drill guide 61, and which is positioned across the distal bone end by an axis- or line-referencing assembly, discussed more fully below. In this embodiment the line-referencing assembly is implemented by a simple pair of viewing apertures or slots 65 in the body 60. As illustrated, the body 60 has been placed by the surgeon so that the apertures 65 are directly over a line or pair of marks 25a, 25b which are previously scribed by the surgeon to mark the projection of the epicondylar axis on the distal bone surface. So positioned, the body 60 places the drill guide holes 61 on the axis. As further shown, the body includes size graduations for the medial/lateral sizing of the femoral prosthetic component, which are arranged as a stepped array 68 of scale markings around the circumference of the body 60, allowing the surgeon to separately size the medial and lateral lobes of the femoral ending by viewing the peripheral outline against the scale markings.

Figure 2:
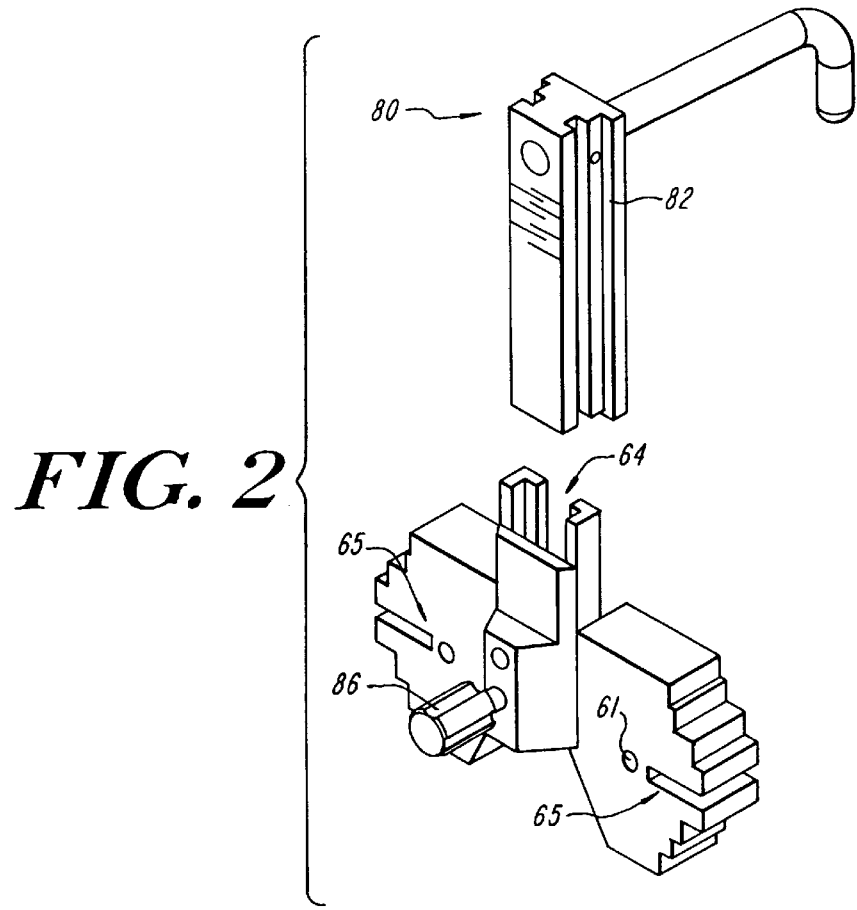
FIG. 2 is an exploded perspective view of the tool shown in FIG. 1 illustrating relevant features.

The body 60 rides on a vertical post or rail 82 which forms a part of an A/P positioning assembly 80, configured as a cortex arm 84 and stylus 84a as discussed further below. As shown in FIG. 2, the post 82 has a stepped cross section, forming a slide rail for uniaxial sliding movement in a T-slot or mating groove 64 that is formed in the body 60. Thus, with the cortex hook 84, 84a positioned on the femoral shaft and the knee in flexion, the body 60 slides vertically, corresponding to the A/P direction as positioned on the femur. A locking screw 86 fixes the A/P distance setting of the drill guide body 60. As further shown schematically in FIG. 3, the cortex arm 84 in some embodiments may be configured to slide in the direction 85 through its mounting aperture in the post 82, so that the tip 84b of the stylus may be brought into position immediately behind the terminal protuberances of the distal femur.

The slidable carriage of the drill positioning guide 60 on the post 82 of which the A/P position is set, allows the positioning pin holes for a prosthesis and/or preparatory cutting blocks to be laid out and drilled on the bone end in the correct A/P offset while the body 60 is simultaneously oriented by the epicondylar axis sighting assembly 65 in alignment along the epicondylar axis. As further shown in FIGS. 1 and 2, a first set of sizing graduations aid 68a, 68b and a second set of graduations 88 aid in determining an appropriate size femoral component, or in adjusting the size, by reference to the medial/lateral and A/P position of the assembly on the resected end surface 21. Thus, the component size may be estimated taking into account the relative extent of the existing features.

Thus it will be seen that the drill positioning body of the tool 100 may be freely moved across the distal end of the femur and as shown in FIG. 1, permit visualization of the femoral shape in relation to the various settings or graduations of the tool and simultaneously perform sizing and A/P positioning. Advantageously, as shown in the top view of FIG. 4, a pair of positioning barbs 61a, 61b project slightly from the posterior (bone contacting) face of the body 60 so that once placed in an appropriate position, a slight tap or pressure will fix the body and prevent further sliding or rotation, thus stably setting the cutting tool position.

Figure 3:
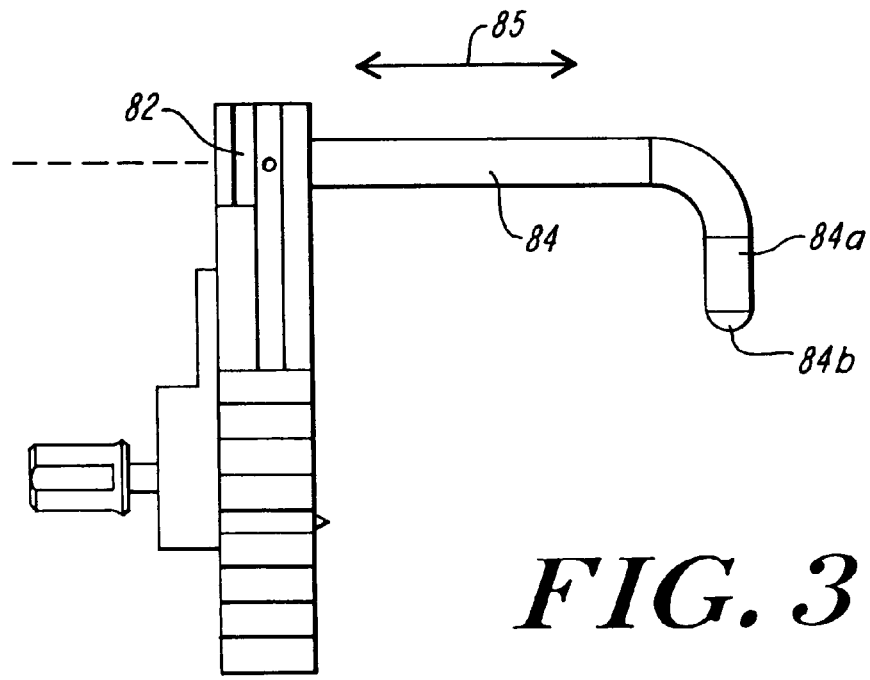
FIG. 3 is a side plan view of the prototype embodiment shown in FIG. 2.
Figure 4:
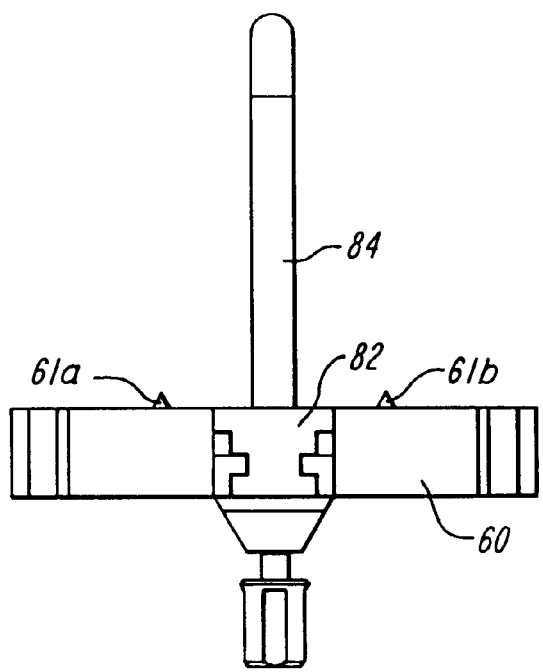
FIG. 4 is a top plan view of that embodiment.

As further shown in the side and top plan views of FIGS. 3 and 4, the cortex positioning bar 84 extends transversely to the plane of the tool alignment body 60 from the central rail or post 82. In accordance with one aspect of the present invention, this arm provides a further sighting or referencing feature for aligning the assembly with respect to the bone. It will be observed that the contact point 84b at the tip of the stylus 84a essentially suspends the body 60 on the arm 84 so that it may be rocked or shifted.

In accordance with a further method of the present invention, the bar 84 is positioned so that it rests in the trochlear notch of the femur, between the epicondyles, and the plate is shifted side-to-side, so that the bar 84 becomes aligned more closely along the groove normally tracked by the patella. In accordance with this aspect of the method and alignment tool of the present invention, the cortex bar 84 is first set at a minimal A/P size position, for example by sliding post 82 in the tracking groove 64 of body 60 to a small size or low size graduation mark on the scale 88, thus making the drill positioning sizing body 60 ride very close to the arm. The arm 84 is then nestled down into the patellar notch of the femur and brought into longitudinal alignment with the groove. The body 60 then lies centered in a position for optimal tracking of the patellar component of the joint. The body 60 may then be raised or lowered along the post 82 until it is approximately centered with respect to the A/P direction on the end of the femur, as illustrated in FIG. 1. The graduation scale 88 will then read the correct A/P prosthesis size. Moreover, the respective left and right sets of medial/lateral femoral component size designations 68a, 68b will then display the optimal size femoral component as determined from the bone geometry on the left and right sides of the center post. In the illustrated embodiment, the odd size graduations are indicated on the upper steps, and the even sizes on the lower steps, to accommodate a greater number of specific sizes in the limited horizontal range between the lowest (1.5) and the highest (6.0) femoral component size graduations. Other graduation schemes may be used, for example placing the numbers at the ends of lines which curve obliquely out to the edges of the body 60. Thus, for example, when shifted to one side or the other to follow the trochlear groove with the cortex hook, the bone may well be asymmetrically positioned and indicate a size three component on the medial edge and a size five component on the lateral edge, or show some similar discrepancy between optimal size indications. The foregoing feature allows the tool to undergo a forced lateral translation in order to select and position a femoral component to achieve optimal patellar tracking in view of the geometry of the bone. Advantageously, the fit of the standard size femoral components may be visually observed in relation to the medial epicondyle, the lateral epicondyle, and the trochlear notch so that adjustments to suit the geometry of the particular bone are readily made before positioning the barbs 61a, 61b and placing the drill holes 61 which will determine all subsequent cuts and chamfers.

While the foregoing description described a method of fitting wherein initially the cortex arm 84 is positioned for optimal patellar tracking, the tool of the present invention may also be used by first positioning the body 60 symmetrically on the end face of the femur, and then using the A/P positioning assembly 80 simply to determine the correct A/P size. It should be noted that the drill guide holes 61a, 61b illustrated in FIG. 1 correspond to a pair of positioning pins having a fixed spacing as used for example by one prosthesis manufacturer in all sizes of a line of femoral components. Those skilled in the art will recognize that this system employs a sequence of cutting blocks and other tools for preparing subsequent chamfers and faces of the bone termination which are also set, justified or otherwise positioned by the same two pin locating holes. However, the tool locator body 60 may be adapted in other embodiments as a saw cut guide rather than a drill guide, or both, in order to position a slot or other cut feature which similarly functions to orient and position one or more cutting blocks. Thus, for example, the tool positioning jig of the present invention may be configured for those prosthesis installation systems which rely upon first forming a slot parallel to or transverse to a given positioning axis, or first creating an anterior or posterior resection.

Thus, in accordance with several advantageous features achieved by the foregoing construction, a single tool permits component sizing while positioning the initial tool cut with respect to the epicondylar axis; and further the tool is able to undergo a range of movement to accommodate adjustments with respect to lateral position and central tracking while sizing the femoral component. By allowing direct measurement or consideration of these various features before fixedly positioning an initial geometry-determining cut, the tool greatly simplifies the procedure of preparing the femur for receiving a prosthetic component, and reduces the risk of performing a standard cut that seriously mismatches the prosthesis placement onto the existing bone. The flexibility of placement results in part from the use of a sighting structure rather than fixed plates, tables or clamps to set an initial position.

Figure 5A:
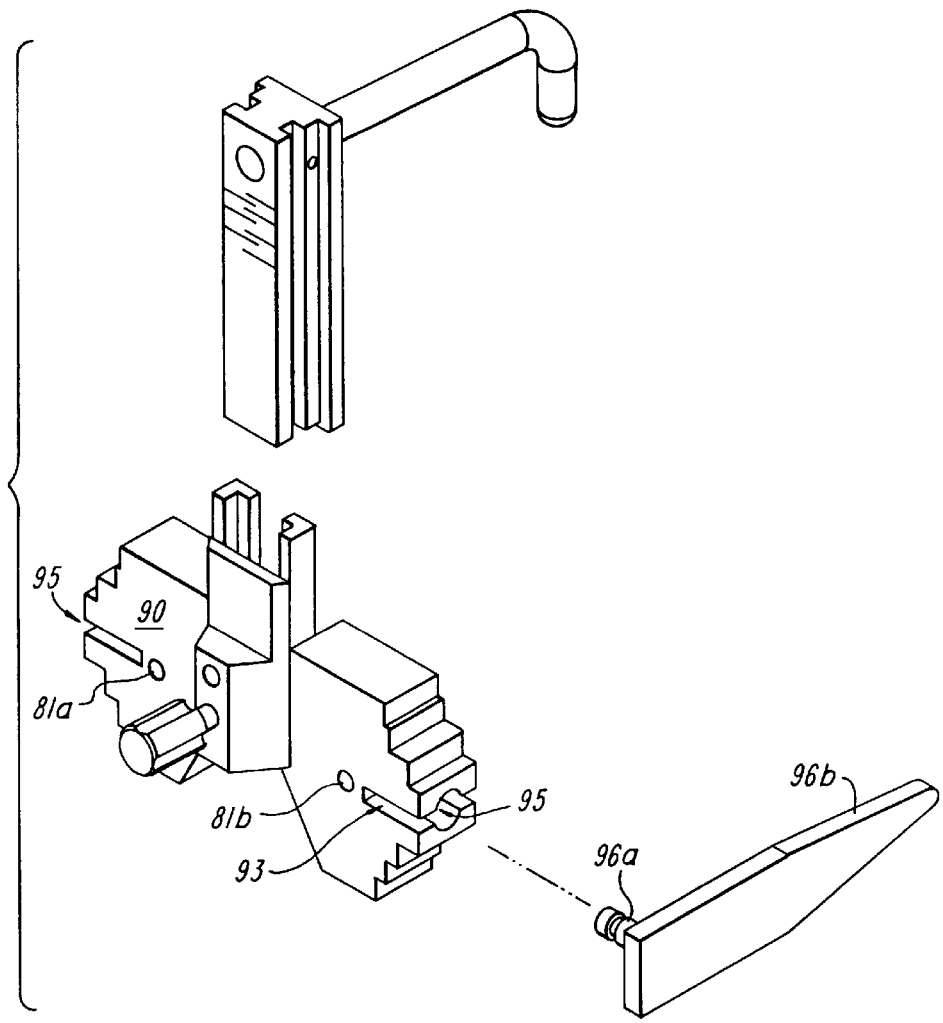
FIGS. 5A and 5B are perspective views of a central body component of a second embodiment of the invention and a subassembly thereof.
Figure 5B:
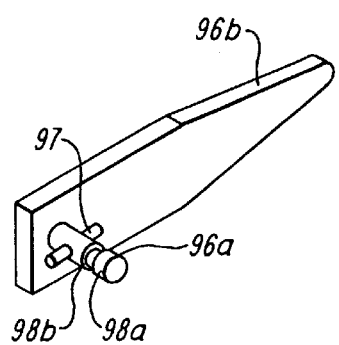

In addition to the sighting slots 65 of the embodiment of FIG. 1, such structures may take various other forms. FIGS. 5A and 5B illustrate a different implementation of the central body for achieving alignment with respect to the epicondylar axis and simultaneously providing medial and lateral femoral component positioning or size designations.

As shown in FIG. 5A, the central body 90 of the component may be formed as a unit which, rather than being aligned by sighting slots 65 (FIG. 1), is provided with medial and lateral positioning bores 95, each of which accommodates a pointer arm 96 that may be moved in and out along the axis of the bore on a mounting shaft 96a so that the tip of the arm 96b is aligned with the prominence of the corresponding epicondyle. The two arms 96 thus position the body 90 parallel to the epicondylar axis. As further shown in FIG. 5B, a cross pin 97 extends through each shaft 96a to ride in a corresponding horizontal slot 93 that extends across the bore 95, so that the arm extends in a fixed direction across the plane of the body and does not rotate about the shaft 96a. This assures that when the arms are visually aligned with the epicondylar prominences or centers, the body 90 is oriented along the epicondylar axis.

In this embodiment, a series of detente notches or sizing marks 98a . . . 98d on the shaft 96a indicate the position of the arm, and thus the offset to one or the other side of the body 90 when so positioned. Thus again, the assembly may be flexibly positioned on the end face of the femur and allow an appropriate component size to be selected based upon each of the medial and lateral aspects of the bone ending. As in the first embodiment, the body 90 slides on the A/P positioning assembly, and may be positioned with respect to the trochlear groove before determining the medial/lateral sizing. Furthermore, with this embodiment the surgeon is not required to first mark or scribe a line on the distal femoral resected surface 21. Instead, the pointer arms 96 may be visually aligned with, or positioned close to or exactly on, the centers of the epicondyles to orient the tool guide body 90. Thus an articulated caliper is configured to align on the opposed medial and lateral epicondylar centers while supporting the template in alignment at the bone surface 21.

When the proper fit is achieved, holes are drilled into the distal resected femur using the drill positioning guide holes 81a, 81b. The device is then removed, and the surgical procedure continues using standard A/P cutting blocks pinned in the two drill holes so made.

This completes a description of a basic embodiment of alignment and sizing tool of the present invention and its mode of use in setting an initial position and sizing the prosthetic component. It will be appreciated that by providing these several capabilities in a single instrument, separate adjustments or checks against different landmarks, previously requiring extensive time for setting up and tedious repositioning of tools, are replaced, by a simplified overall procedure for preparing the bone to fit a prosthesis. The tool is usable even when a previous arthroplasty has removed anterior, distal or posterior reference features of the distal femur, and it allows the surgeon to check patellar tracking as well as the prosthesis sizing and fit, before making any determinative cuts. Among the advantages of the structure of the device, rather than eyeballing or simply marking an axis to use as a confirmatory check or secondary adjustment data, the present invention advantageously provides a direct and positive positioning for a standard set of cutting blocks to achieve a fit compatible with the natural articulation geometry and to adjust that fit for proper patellar tracking. This results in a flexible preparation procedure, and permits several practical adjustments to be carried out with enhanced control or perception of the tensioning and positioning of necessary components.

The invention being thus disclosed in representative prototype embodiments, further variations and modifications will occur to those skilled in the art, and all such variations and modifications are considered to be within the scope of the invention has set forth herein and defined by the claims appended hereto.

What is claimed is:

1. A jig for performing cuts to prepare a bone for mounting a prosthetic joint component or the like, such jig comprising:

a central body including a sizing jig for indicating prosthesis sizes together with a tool guide for setting position of a tool to cut a position-determining feature on the bone, said central body further including a sighting assembly configured for orienting the central body with respect to an epicondylar axis of the bone; and an A/P positioning assembly for setting an A/P position of the central body against the end of the bone;

whereby the position of the tool cut is simultaneously positioned with respect to A/P offset and aligned with respect to the epicondylar axis.

2. A jig according to claim 1, wherein the central body includes a template for determining prosthesis size for the bone.

3. A jig according to claim 2, wherein the central body is slidable along a cross direction for shifting the tool guide so as to selectively adjust placement of the position-determining feature.

4. A jig according to claim 1, wherein the A/P positioning assembly includes a cortex hook assembly and the central body is suspended from said assembly for sliding movement in an anterior-posterior direction.

5. A jig according to claim 1, wherein the A/P positioning assembly includes a cortex arm that is alignable with a trochlear groove by manually shifting position of the central body to position a femoral prosthetic component to optimize patellar tracking.

6. A jig according to claim 5, wherein the central body includes a sizing indicator to indicate prosthesis fit as the jig simultaneously aligns relative to both the epicondylar axis and the trochlear groove.

7. A jig according to claim 1, having a projection extending along a substantially normal direction from the central body, and wherein the jig is alignable by manual lateral displacement while seating the projection in a trochlear groove to thereby adjust position of the central body relative to two distinct bone features before fixing its position.

8. A jig according to claim 1, further comprising an A/P contact gauge for indicating A/P offset, and wherein the jig is manually movable along the epicondylar axis as the contact gauge touches the bone to set a prosthesis position for enhanced patellar tracking.

9. A jig according to claim 1, wherein the central body includes projecting prongs for temporarily securing the member in a visually determined position prior to cutting the position-determining feature.

10. A tool according to claim 1, wherein the tool guide is a drill guide for positioning a spaced set of drill holes in an end surface of the bone to secure a cutting block.

11. A tool according to claim 1, wherein the sighting assembly includes first and second arms extending from the central body and being alignable to without engaging respective first and second opposed epicondylar regions of the bone, and coupled to the cross member such that when aligned with said opposed regions the cross member is oriented along the epicondylar axis.

12. A tool according to claim 1, wherein the sighting assembly includes a slot or window in the central body alignable with an epicondylar axis marking.

* * * * *